(12) United States Patent
Xu et al.

(10) Patent No.: US 10,646,179 B2
(45) Date of Patent: May 12, 2020

(54) MULTI-ENERGY SPECTRUM X-RAY IMAGING SYSTEMS AND METHODS FOR RECOGNIZING ARTICLE USING MULTI-ENERGY SPECTRUM X-RAY IMAGING SYSTEM

(71) Applicant: NUCTECH COMPANY LIMITED, Haidian District, Beijing (CN)

(72) Inventors: Guangming Xu, Beijing (CN); Bicheng Liu, Beijing (CN); Ziran Zhao, Beijing (CN); Lan Zhang, Beijing (CN); Jianping Gu, Beijing (CN)

(73) Assignee: NUCTECH COMPANY LIMITED, Haidian District, Beijing (CN)

( * ) Notice: Subject to any disclaimer, the term of this patent is extended or adjusted under 35 U.S.C. 154(b) by 224 days.

(21) Appl. No.: 15/720,502

(22) Filed: Sep. 29, 2017

(65) Prior Publication Data
US 2018/0153493 A1    Jun. 7, 2018

(30) Foreign Application Priority Data

Dec. 7, 2016    (CN) .......................... 2016 1 1121287

(51) Int. Cl.
  *A61B 6/00*    (2006.01)
  *A61B 6/02*    (2006.01)
  (Continued)

(52) U.S. Cl.
  CPC .............. *A61B 6/482* (2013.01); *A61B 6/02* (2013.01); *A61B 6/4014* (2013.01);
  (Continued)

(58) Field of Classification Search
  CPC .... G01V 5/0075; A61B 6/482; A61B 6/4014; A61B 6/02
  See application file for complete search history.

(56) References Cited

U.S. PATENT DOCUMENTS

| 6,501,828 B1 | 12/2002 | Popescu |
| 2006/0203960 A1 | 9/2006 | Schlomka et al. |

(Continued)

FOREIGN PATENT DOCUMENTS

| CN | 1751250 A | 3/2006 |
| CN | 1847833 A | 10/2006 |

(Continued)

OTHER PUBLICATIONS

Extended European Search Report for corresponding European Patent Application No. 17194171.9, dated May 11, 2018, 8 pages.

(Continued)

*Primary Examiner* — Yara B Green
(74) *Attorney, Agent, or Firm* — Merchant & Gould P.C.

(57) ABSTRACT

The present disclosure provides a method for recognizing an article using a multi-energy spectrum X-ray imaging system and a multi-energy spectrum X-ray imaging system. The method comprises: recognizing an application scenario and/or priori information of the article; selecting a parameter mode suitable for the article from a plurality of parameter modes stored in the multi-energy spectrum X-ray imaging system based on the recognized application scenario and/or priori information; and recognizing the article using the selected parameter mode, wherein the plurality of parameter modes are obtained by optimizing system parameters of the multi-energy spectrum X-ray imaging system under a specific condition using a training sample library for various articles.

15 Claims, 4 Drawing Sheets

(51) Int. Cl.
*G01V 5/00* (2006.01)
*A61B 6/06* (2006.01)

(52) U.S. Cl.
CPC .............. *G01V 5/0041* (2013.01); *A61B 6/06* (2013.01); *A61B 6/4241* (2013.01)

(56) References Cited

U.S. PATENT DOCUMENTS

| | | |
|---|---|---|
| 2007/0025502 A1 | 2/2007 | Bussho |
| 2008/0056444 A1 | 3/2008 | Skatter et al. |
| 2013/0039462 A1* | 2/2013 | Morton ................ G01V 5/0041 378/57 |
| 2014/0282624 A1* | 9/2014 | Holt ........................ G06F 9/542 719/318 |
| 2014/0333326 A1 | 11/2014 | Peschmann et al. |
| 2015/0164457 A1* | 6/2015 | Nett ....................... A61B 6/542 703/13 |
| 2015/0209599 A1* | 7/2015 | Schlosser ............. A61N 5/1049 600/427 |

FOREIGN PATENT DOCUMENTS

| | | |
|---|---|---|
| CN | 101558327 A | 10/2009 |
| CN | 102007432 A | 4/2011 |
| CN | 203244404 U | 10/2013 |
| CN | 104374785 A | 2/2015 |
| JP | 2001-291090 A | 10/2001 |
| WO | 2009/106857 A2 | 9/2009 |
| WO | 2016/074365 A1 | 5/2016 |

OTHER PUBLICATIONS

International Search Report and Written Opinion of the International Searching Authority for corresponding International Patent Application No. PCT/CN2017/101345 dated Nov. 29, 2017, 15 pages.

Gorecki, A. et al., "Comparing performances of a CdTe X-ray spectroscopic detector and an X-ray dual-energy sandwich detector", Journal of Instrumentation, Institute of Physics Publishing, 8(11): 1-21 (2013).

Chinese Office Action for corresponding Chinese Patent Application No. 201611121287.9 dated Dec. 31, 2019, 10 pages.

* cited by examiner

MULTI-ENERGY SPECTRUM X-RAY IMAGING SYSTEMS AND METHODS FOR RECOGNIZING ARTICLE USING MULTI-ENERGY SPECTRUM X-RAY IMAGING SYSTEM

CROSS-REFERENCE TO RELATED APPLICATION(S)

This application claims a priority to Chinese Patent Application No. 201611121287.9, filed on Dec. 7, 2016, which is incorporated herein by reference in their entireties.

TECHNICAL FIELD

The present disclosure relates generally to the field of radiation imaging, and more particularly, to multi-energy spectrum X-ray imaging systems and methods for recognizing an article using a multi-energy spectrum X-ray imaging system.

BACKGROUND

Radiation imaging technology is widely used in security inspection and medical fields, and the article recognition capability of imaging systems is an important criterion for measuring system indicators.

With the continuous development of photon counting detector technology such as CZT, multi-energy spectrum imaging has many advantages in reducing radiation dose and improving the article recognition capability etc., and has a wide application prospect. The multi-energy spectrum imaging can divide an energy spectrum of received X-rays into a plurality of energy regions and count them separately to obtain ray attenuation information corresponding to different energy regions. Compared with the conventional dual-energy imaging, the multi-energy spectrum imaging substantially eliminates the overlapping between the energy spectrums, and has better energy discriminability between different energy regions, thereby significantly improving the article recognition capability of the system, while dividing the energy spectrum into more energy regions as required, and providing conditions for the introduction of more energy information.

A number of energy regions into which an energy spectrum is divided through existing multi-energy spectrum imaging may be from three to five in the early stage to several to 256 at present. In general, due to the use of more energy information, more refined energy spectrum division can not only bring higher article recognition capability for the system, but also cause higher cost and more difficulty for the system design and data processing.

French research institution CEA-Leti proposed that in a case that there are only a small number of energy regions, the article recognition capability of the system after optimizing an energy spectrum threshold can be significantly improved compared with the equal division of an energy spectrum. For a selected target material, an optimized five-energy region system can also have a higher article recognition capability, but the optimized threshold parameters may only be applied to recognition of materials that are closer to the selected target material. If a more refined energy region division is used, the system has a stronger applicability for the recognition of different materials, but this will result in a greater system overhead. At present, the optimization methods involved in the research of parameter optimization are mainly a CIP method and a CRC method based on a recognition process. Parameters obtained by different optimization methods are very close.

For a particular application scenario, in most cases, there is no need for a very refined energy region division, but a few divided energy regions are used while preforming optimization and adjustment on the threshold parameters, which can also enable the system to achieve a better article recognition effect.

SUMMARY

In order to achieve the above purposes, in a first aspect of the present disclosure, there is disclosed a method for recognizing an article using a multi-energy spectrum X-ray imaging system, comprising;

recognizing an application scenario and/or priori information of the article;

selecting a parameter mode suitable for the article from a plurality of parameter modes stored in the multi-energy spectrum X-ray imaging system based on the recognized application scenario and/or priori information; and recognizing the article using the selected parameter mode, wherein the plurality of parameter modes are obtained by optimizing system parameters of the multi-energy spectrum X-ray imaging system under a specific condition using a training sample library for various articles.

Preferably, the specific condition comprises a highest detection rate, a lowest false positive rate, or largest discriminability.

Preferably, the system parameters comprise: an energy value of an X-ray source, a number of divided energy regions and a corresponding energy threshold, a scanning speed, and a radiation dose value.

Preferably, the plurality of parameter modes comprise a first parameter mode for baggage and human body inspection and a second parameter mode for vehicles/containers.

Preferably, the plurality of parameter modes comprise a common parameter mode and a high performance parameter mode.

Preferably, the method further comprises:

switching the selected parameter mode from the common parameter mode to the high performance parameter mode, when the selected parameter mode is the common parameter mode and it is recognized that there is a high probability of the article being a prohibited article using the selected parameter mode.

According to a second aspect of the present disclosure, there is disclosed a multi-energy spectrum X-ray imaging system for recognizing an article, comprising:

an X-ray source configured to generate X-rays under the control of a scanning controller;

the scanning controller configured to control the X-ray source according to a selected parameter mode;

a detector configured to receive X-rays which are emitted from the X-ray source and are transmitted or scattered through the article and convert them into an output signal;

a processor configured to: recognize an application scenario and/or priori information of the article, select a parameter mode suitable for the article from a plurality of parameter modes stored in the multi-energy spectrum X-ray imaging system based on the recognized application scenario and/or priori information, and receive an output signal from the detector and recognize the article using the output signal; and a memory configured to store the plurality of parameter modes, wherein the plurality of parameter modes are obtained by optimizing system parameters of the multi-energy spectrum X-ray imaging system under a specific condition using a training sample library for various articles.

Preferably, the specific condition comprises a highest detection rate, a lowest false positive rate, or largest discriminability.

Preferably, the system parameters comprise: an energy value of an X-ray source, a number of divided energy regions and a corresponding energy threshold, a scanning speed, and a radiation dose value.

Preferably, the plurality of parameter modes comprise a first parameter mode for baggage and human body inspection and a second parameter mode for vehicles/containers.

Preferably, the plurality of parameter modes comprise a common parameter mode and a high performance parameter mode.

Preferably, the processor is further configured to switch the selected parameter mode from the common parameter mode to the high performance parameter mode, when the selected parameter mode is the common parameter mode and it is recognized that there is a high probability of the article being a prohibited article using the selected parameter mode.

According to a third aspect of the present disclosure, there is disclosed a computer-readable medium comprising instructions that, when executed by a processor, perform operations of:

recognizing an application scenario and/or priori information of the article;

selecting a parameter mode suitable for the article from a plurality of parameter modes stored in the multi-energy spectrum X-ray imaging system based on the recognized application scenario and/or priori information; and recognizing the article using the selected parameter mode, wherein the plurality of parameter modes are obtained by optimizing system parameters of the multi-energy spectrum X-ray imaging system under a specific condition using a training sample library for various articles.

Preferably, the specific condition comprises a highest detection rate, a lowest false positive rate, or largest discriminability.

Preferably, the system parameters comprise: an energy value of an X-ray source, a number of divided energy regions and a corresponding energy threshold, a scanning speed, and a radiation dose value.

Preferably, the plurality of parameter modes comprise a first parameter mode for baggage and human body inspection and a second parameter mode for vehicles/containers.

Preferably, the plurality of parameter modes comprise a common parameter mode and a high performance parameter mode.

Preferably, the computer-readable medium further comprises instructions that, when executed by a processor, perform operations of: switching the selected parameter mode from the common parameter mode to the high performance parameter mode, when the selected parameter mode is the common parameter mode and it is recognized that there is a high probability of the article being a prohibited article using the selected parameter mode.

BRIEF DESCRIPTION OF THE DRAWINGS

Other details, aspects, and advantages of the present disclosure will become apparent from the following description of exemplary embodiments taken in conjunction with the accompanying drawings, in which.

The drawings do not show all of the circuits or structures of the embodiments. The same reference numerals throughout the drawings refer to like or similar parts or features.

DETAILED DESCRIPTION

The specific embodiments of the present disclosure will be described in detail below. It should be noted that the embodiments herein are used for illustration only, without limiting the present disclosure. In the description below, a number of specific details are explained to provide better understanding of the present disclosure. However, it is apparent to those skilled in the art that the present disclosure can be implemented without these specific details. In other instances, well known circuits, materials or methods are not described specifically so as not to obscure the present disclosure.

Throughout the specification, the reference to "one embodiment," "an embodiment," "one example" or "an example" means that the specific features, structures or properties described in conjunction with the embodiment or example are included in at least one embodiment of the present disclosure. Therefore, the phrases "in one embodiment," "in an embodiment," "in one example" or "in an example" occurred in various positions throughout the specification may not necessarily refer to the same embodiment or example. Furthermore, specific features, structures or properties may be combined into one or more embodiments or examples in any appropriate combination and/or sub-combination. Moreover, it should be understood by those skilled in the art that the drawings provided herein are for illustration purposes, and not necessarily drawn to scale. The term "and/or" used herein means any and all combinations of one or more listed items.

Figure 1:
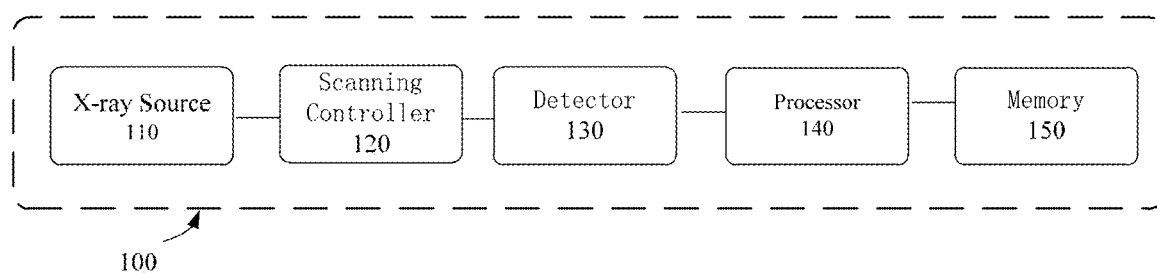
FIG. 1 shows a schematic diagram of a multi-energy spectrum X-ray imaging system for recognizing an article according to an embodiment of the present disclosure.

FIG. 1 shows a multi-energy spectrum X-ray imaging system 100 with adjustable parameters according to an embodiment of the present disclosure. The multi-energy spectrum X-ray imaging system 100 is mainly composed of an X-ray source 110, a scanning controller 120, a detector 130, a processor 140, and a memory 150.

The X-ray source 110 may be any device that acquires X-rays such as isotopes, light machines, accelerators, and the like. The obtained X-rays may have a single or multiple energy spectrum distributions, and the collimated X-rays may be a fan-shaped beam, a pencil-shaped beam, or other shaped beams. In one example, the X-ray source generates X-rays under control of the scanning controller 120.

The scanning controller 120 controls an entire scanning procedure, and controls and adjusts an energy value E of the X-ray source 110, a number n of divided energy regions and a corresponding energy threshold $[E_i^{min}, E_i^{max}]$, a scanning speed v, a radiation dose value d, and other system parameters at any time, based on a selected parameter mode.

Figure 2:
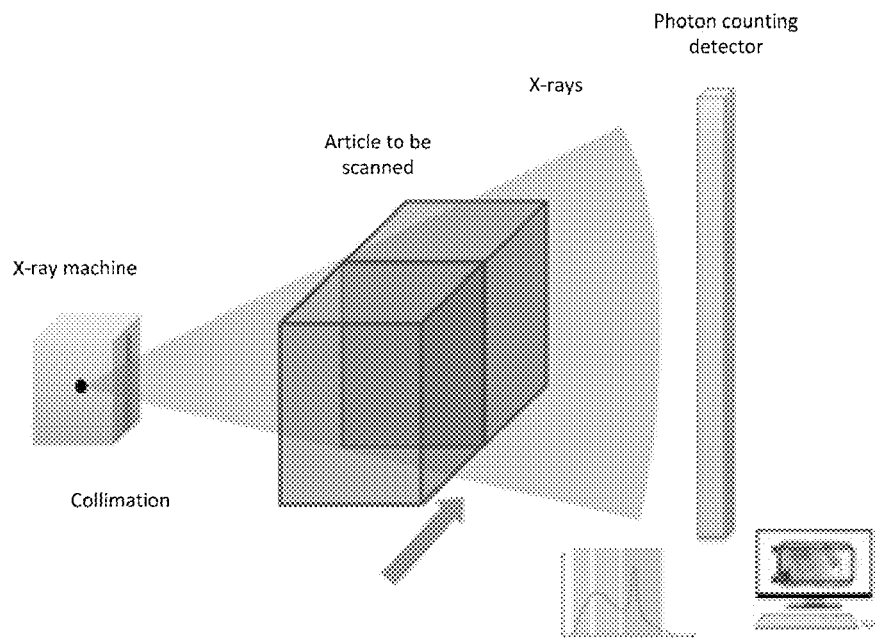
FIG. 2 shows a schematic diagram of recognizing an article using a multi-energy X-ray spectrum imaging system according to an embodiment of the present disclosure.

A photon counting detector, which may be arranged in a linear array or a multi-layer linear array, such as a CZT detector arranged in a linear array, or a detector which may be arranged in an area array or a multi-layer area array, may be used as the detector 130. The detector receives X-rays which are emitted from the X-ray source 110 and are transmitted or scattered through the article and converts them into an output signal, as shown in FIG. 2.

Figure 3:
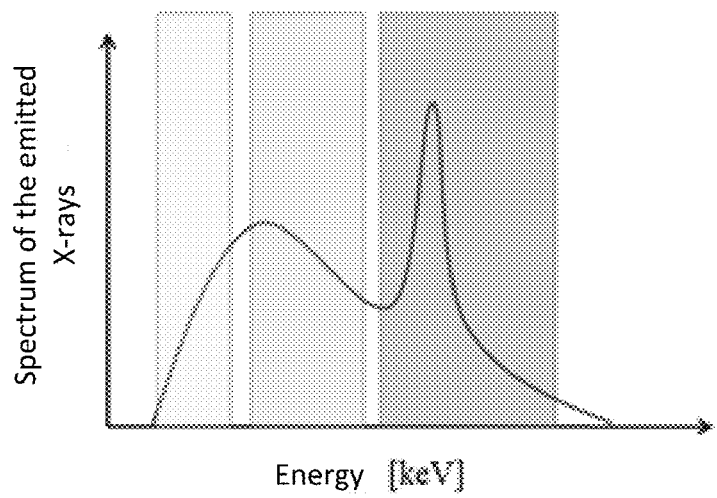
FIG. 3 shows a schematic diagram of energy spectrum threshold division according to an embodiment of the present disclosure.

The processor 140 recognizes an application scenario and/or priori information of the article and selects a parameter mode suitable for the article from a plurality of parameter modes stored in the memory 150 based on the recognized application scenario and/or priori information. Depending on a manner in which an energy spectrum of the rays is divided, the processor 140 may employ different ways to achieve the acquisition and division of photon energy information. In a case that there are less than 15 energy regions, a specific number of divided energy regions may be 6, 7, 9, 10, 12 and so on, divided energy threshold ranges are not uniform, and the energy regions may not be adjacent to each other (as shown in FIG. 3); and in a case that there are no less than 15 energy regions, the specific number of divided energy regions may be 15, 20, 32, 48, 50, 72 and so on. The processor 140 receives the output signal from the detector 130, stores the data of the respective divided energy regions separately, and analyzes the multi-energy spectrum data to obtain an atomic number Z and a mass thickness t of the article under test, output a result of recognizing the article and colorize it to display a color image.

The memory 150 stores a plurality of parameter modes obtained by optimizing system parameters of the multi-energy spectrum X-ray imaging system under a specific condition using a training sample library for various articles. Each parameter mode corresponds to a number of optimized system parameters. In the following, a method of optimizing the system parameters will be described.

First of all, positive and negative training sample libraries are established, and then the system parameters are optimized based on conditions such as a highest detection rate, a lowest false positive rate, or largest discriminability etc., which should include at least optimization of an energy region division manner, an energy threshold and a radiation dose value. The training sample libraries for parameter optimization may be obtained by scanning selected various article materials with different thicknesses, or by a Monte Carlo simulation method. In a case of recognition of a specific prohibited article a (e.g., solid explosives TNT and RDX) and an article b similar to the prohibited article a (e.g., polymer material POM) and N divided energy regions, a feasible optimization scheme is to define discriminability DC between different materials to find system parameters which make the discriminability largest. The discriminability may be calculated by the following equation (1):

$$DC_{ab} = \sqrt{\sum_{i=1}^{N} \frac{(\overline{T_i^a} - \overline{T_i^b})^2}{\sigma(T_i^a)^2 + \sigma(T_i^b)^2}} \quad (1)$$

wherein, $\overline{T_i^a}$ and $\overline{T_i^b}$ are mean values of transparency values obtained by multiple measurements of the prohibited article a and its similar article b, respectively. $\sigma(T_i^a)^2$ and $\sigma(T_i^b)^2$ are variances of the transparency values obtained by multiple measurements of the prohibited article a and its similar article b, respectively, and N is the number of the energy regions.

The following example illustrates a method that can be used for parameter optimization:

1, establishing Monte Carlo simulation, according to various parameters of the multi-energy spectrum imaging system;

2, setting a number of divided energy regions, for example, 6, and setting a radiation dose value of the system, including at least two preset modes, i.e., a high dose mode and a low dose mode;

3, simulating a multi-energy spectrum imaging process, establishing sample library data through a variety of selected materials with different thicknesses, and saving energy spectrum imaging information;

4, calculating discriminability DC for recognition of a certain selected material/prohibited article;

5, firstly, traversing various possible energy region division manners using a large step size such as 5 keV, to find an energy region division manner which makes the discriminability largest;

6, scanning threshold parameters within a certain range using a step size of 1 keV based on the above result, to find optimized system parameters which make the discriminability largest as a parameter module for saving;

7, repeating the above processes for other types of prohibited articles;

8, changing the preset number of divided energy regions, and repeating the above processes; and 9, verifying a specific sample in the multi-energy spectrum imaging system, and fine-adjusting the parameters according to practical situations.

Through the above processes, parameter modes corresponding to various types of articles are stored in the multi-energy spectrum imaging system.

In the following, several preferred embodiments for recognizing an article using a multi-energy X-ray imaging system according to the present disclosure are given.

In a first preferred embodiment, a corresponding system parameter mode is selected according to a focus of article recognition of the multi-energy spectrum system. Specifically, for a variety of different application scenarios, such as subway, airport, customs, etc., types of target prohibited articles on which the multi-energy spectrum system focuses are also different. Further, the same application scenarios will have different focuses. Switching is performed between parameter modes to adjust the system's corresponding parameters according to different prohibited articles on which the system focuses. Several commonly used system parameter modes M1, M2, M3 . . . are preset in advance to facilitate the system to switch at any time.

For example, for vehicle scanning, baggage scanning and human body inspection, X-rays with different energy spectrums and doses and different energy spectrum division parameters are required to be used. In an application scenario in which a thin organic matter is needed to be distinguished such as baggage and human body inspection, it is needed to divide a low energy region of an energy spectrum into more energy regions, in which case an M1 mode is used. In another application scenario such as vehicle/container inspection etc., a hided prohibited article has a thicker shelter, and therefore it is needed to properly increase the maximum energy and dose of the X-ray machine, and use a system parameter mode M2 suitable for this condition.

Figure 4:
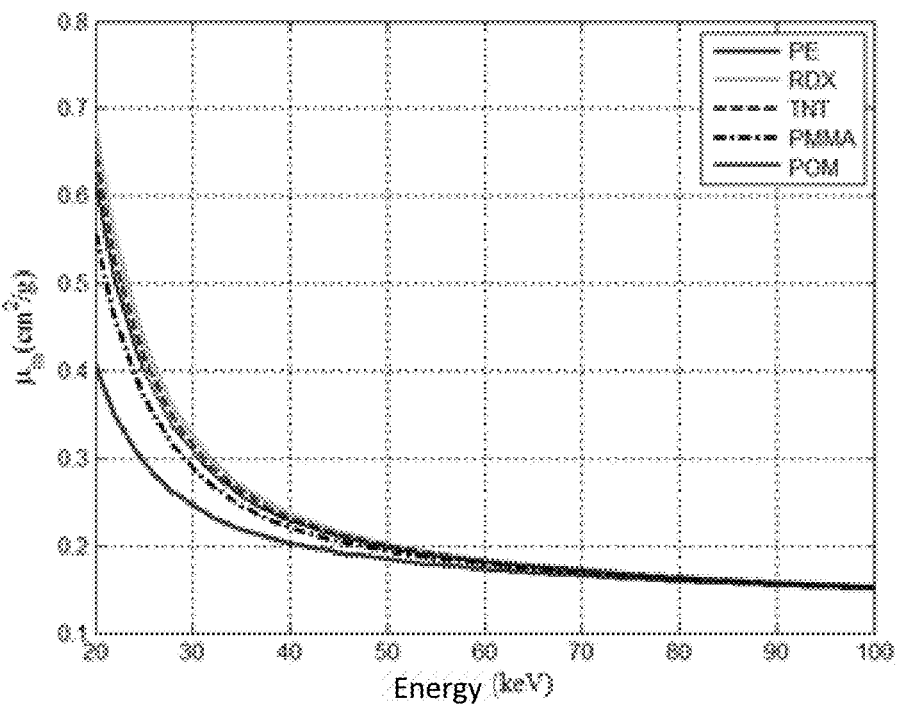
FIG. 4 shows a schematic diagram equivalent mass attenuation coefficient distributions of a common polymer and a typical solid explosive according to an embodiment of the present disclosure.

For example, for recognition of solid explosives, it is needed to distinguish explosives such as TNT, C4, plastic explosives, RDX (hexogen), HMX (Octogen), black powder etc. from common organic materials such as PE, organic glass, POM, PVDF, PTFE etc. In this case, a low energy region of an energy spectrum plays a major role in classification (as shown in FIG. 4), and a more refined energy region division is required for the imaging system. For inspection of liquid explosives, it is needed to pay high attention to distinguishing dangerous liquids such as alcohol, nitroglycerin etc. from safe liquids such as water, carbonated drinks, dairy products, fruit juice and honey etc. In this case, in addition to decide atomic number information, auxiliary density Information is also required to aid in the inspection, where a density of the liquid may be calculated in combination with geometric information of bottled liquid.

In a second preferred embodiment, a corresponding system parameter mode is selected according to priori information of an article under test.

In the field of security inspection, a corresponding system parameter model is selected according to the available priori information such as customs declaration of luggage compartment, air box or the container cargo to be scanned etc. In the medical field, a corresponding system parameter mode may be selected according to pathological features which are needed to be investigated emphatically of different parts of a patient to be scanned.

For example, in the field of security inspection, for a variety of different types of goods, a plurality of different parameters modes are preset in the system. Before the start of the scanning process, the system switches a scanning device to a preset scanning mode to start the scanning process by understanding the semantic information on the goods to be scanned on the customs declaration, such as type, size, and weight etc. of the goods.

Figure 5:
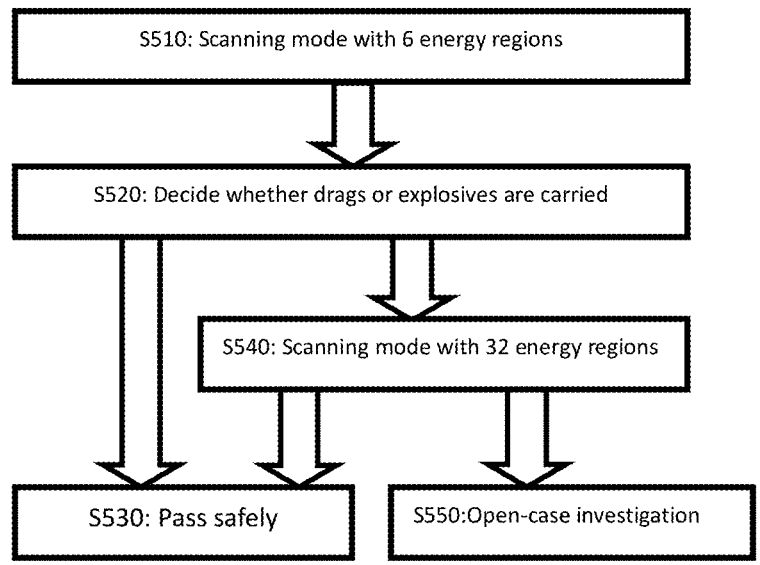
FIG. 5 shows a flow chart of a dual mode multi-energy spectrum X-ray imaging inspection according to an embodiment of the present disclosure.
Figure 6:
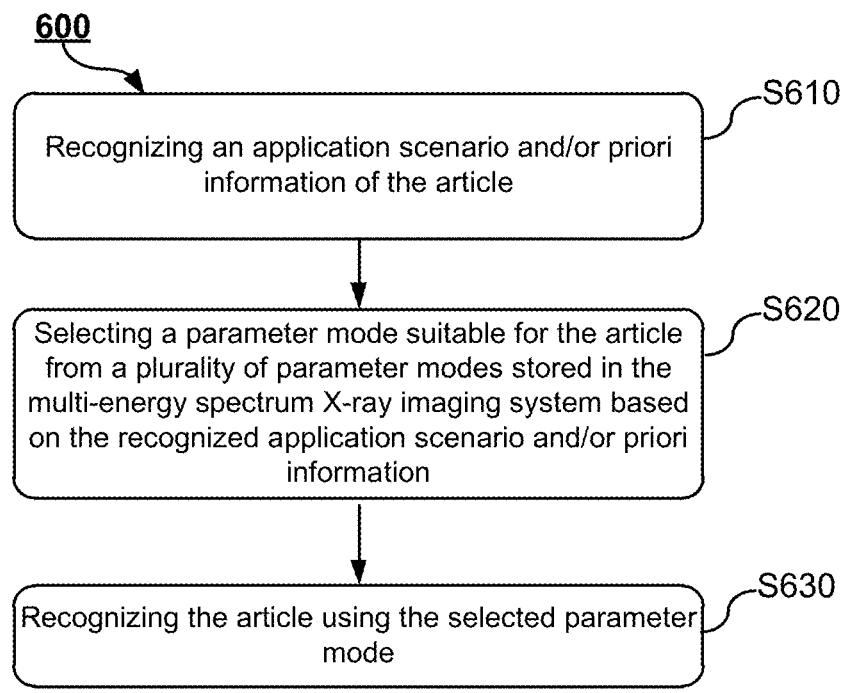
FIG. 6 shows a flow chart of a method for recognizing an article using a multi-energy spectrum X-ray imaging system according to an embodiment of the present disclosure.

In a third preferred embodiment, after scanning in a common mode, switching to a high performance mode is performed to rescan the key suspicious articles or areas, as shown in FIG. 5.

At least two scanning modes with different system parameters and performances should be preset in the scanning device, one of which has common performance and the other has high performance, for example, two modes of dividing the energy spectrum into 6 energy regions and dividing the energy spectrum into 32 energy regions.

Firstly, in step S510, the article under test is scanned in the common scanning mode with 6 energy regions (for example, the energy spectrum division threshold parameter is optimized for recognition of solid explosives). Then, in step S520, a probability p of containing a prohibited article in the article under test is decided in combination with information such as an atomic number Z and a mass thickness t obtained by an article recognition algorithm of multi-energy spectrum imaging. In step S530, for an inspection case where there is a small probability of carrying a prohibited article, the article under test may be safely passed. In step S540, for an inspection case where there is a large probability of carrying a prohibited article, particularly a baggage package containing suspected drug or explosives, the system may be immediately switched to a high performance scanning mode with 32 energy regions. At the same time, a slow scanning speed v may be selected and/or radiation dose d may be increased properly, to rescan the package. In step S550, for a case where it is determined to be highly suspicious prohibited article after the rescanning, open-case inspection may be performed. Another possible scheme is that for a large suspicious area found in scanning a large cargo container, targeted scanning investigation may be performed only on this area after the system is switched to a high performance state. The premise of this scheme is that the common scanning mode has been able to investigate most of the cases.

For a small number of divided energy regions, the parameters of the multi-energy spectrum imaging system are needed to be adjusted for different application scenarios, and a large number of divided energy regions may result in greater system overhead. The present disclosure proposes a multi-energy spectrum X-ray imaging system with adjusted parameters, so that the multi-energy spectrum imaging system can adapt to a variety of different application scenarios and achieve a balance between performance and overhead of the system.

In correspondence with the above-mentioned multi-energy spectrum X-ray imaging system 100, there is also provided a method 600 for recognizing an article using the multi-energy spectrum X-ray imaging system. The method 600 may be performed by the multi-energy spectrum X-ray imaging system 100 described above, and includes the following steps.

In step S610, an application scenario and/or priori information of the article is recognized.

In step S620, a parameter mode suitable for the article is selected from a plurality of parameter modes stored in the multi-energy spectrum X-ray imaging system according to the recognized application scenario and/or priori information, wherein the plurality of parameter modes are obtained by optimizing system parameters of the multi-energy spectrum X-ray imaging system under a specific condition using a training sample library for various articles.

In step S630, the article is recognized using the selected parameter mode.

The method 600 may further comprise switching the selected parameter mode from the common parameter mode to a high performance parameter mode, when the selected parameter mode is a common parameter mode and it is recognized that there is a high probability of the article being a prohibited article using the selected parameter mode.

Figure 7:
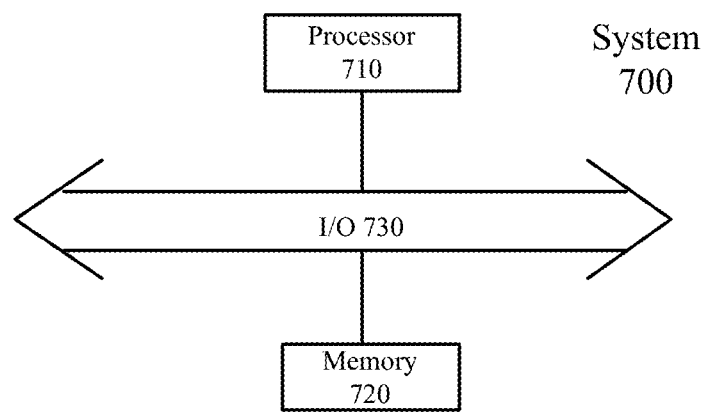
FIG. 7 shows a schematic diagram of a system for recognizing an article using a multi-energy spectrum X-ray imaging system according to an embodiment of the present disclosure.

FIG. 7 shows a schematic diagram of a system 700 for recognizing an article using a multi-energy spectrum X-ray imaging system according to an embodiment of the present disclosure. The system 700 includes a processor 710, such as a digital signal processor (DSP). The processor 710 may be a single device or a plurality of devices for performing different actions of the processes described herein. The system 700 may also include an input/output (I/O) device 730 for receiving signals from other entities or sending signals to other entities.

In addition, the system 700 includes a memory 720 that may have: nonvolatile or volatile memory, such as electrically erasable programmable read-only memory (EEPROM), flash memory, and the like. The memory 720 stores computer readable instructions that, when executed by the processor 710, causes the processor to perform the actions described herein.

Some block diagrams and/or flowcharts are shown in the accompanying drawings. It should be understood that some of the blocks or combinations thereof in block diagrams and/or flowcharts may be implemented by computer program instructions. These computer program instructions may be provided to a processor of a general purpose computer, a dedicated computer, or other programmable data processing device such that these instructions may be create apparatuses for to implement the functions/operation described in these block diagrams and/or flowcharts when executed by the processor.

Thus, the techniques of the present disclosure may be implemented in the form of hardware and/or software (including firmware, microcode, etc.). In addition, the techniques of the present disclosure may take the form of a computer program product on a computer readable medium storing instructions that may be used by an instruction execution system (e.g., one or more processors) or in conjunction with an instruction execution system. In the context of the present disclosure, a computer-readable medium may be any medium capable of containing, storing, transferring, propagating, or transmitting instructions. For example, computer-readable media may include, but are not limited to, electrical, magnetic, optical, electromagnetic, infrared, or semiconductor systems, devices, apparatus, or propagation media. A specific example of the computer-readable medium may comprise: a magnetic storage device such as a magnetic tape or a hard disk (HDD); an optical storage device such as optical disk (CD-ROM); a memory such as a random access memory (RAM) or a flash memory; and/or a wired/wireless communication link.

The above detailed description explains various embodiments of a method for recognizing an article using a multi-energy spectrum X-ray imaging system and a multi-energy spectrum X-ray imaging system by way of illustration, flowcharts and/or examples, numerous embodiments. In a case that such illustration, flowcharts and/or examples include one or more functions and/or operations, it will be understood by those skilled in the art that each of the functions and/or operations in such illustrations, flowcharts, or examples may be individually and/or collectively implemented in a variety of structures, hardware, software, firmware, or substantially any combination thereof. In one embodiment, several portions of the subject matter described in the embodiments of the present disclosure may be implemented via Application Specific Integrated Circuits (ASICs), Field Programmable Gate Arrays (FPGAs), Digital Signal Processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g., as one or more programs running on one or more microprocessors), as firmware, or as virtually any combination thereof, and that designing the circuitry and/or writing the code for the software and/or firmware would be well within the skill of those skilled in the art in ray of this disclosure. In addition, those skilled in the art will appreciate that the mechanisms of the subject matter described herein are capable of being distributed as a program product in a variety of forms, and that an illustrative embodiment of the subject matter described herein applies regardless of the particular type of signal bearing medium used to actually carry out the distribution. Examples of a signal bearing medium include, but are not limited to, the following: a recordable type medium such as a floppy disk, a hard disk drive, a Compact Disc (CD), a Digital Versatile Disk (DVD), a digital tape, a computer memory, etc.; and a transmission type medium such as a digital and/or an analog communication medium (e.g., a fiber optic cable, a waveguide, a wired communications link, a wireless communication link, etc.).

We claim:

1. A method for recognizing an article using a multi-energy spectrum X-ray imaging system, comprising;
   recognizing an application scenario and/or priori information of the article;
   selecting a parameter mode suitable for the article from a plurality of parameter modes stored in the multi-energy spectrum X-ray imaging system based on the recognized application scenario and/or priori information, wherein the plurality of parameter modes comprise a common parameter mode and a high performance parameter mode; and
   recognizing the article using the selected parameter mode, wherein the plurality of parameter modes are obtained by optimizing system parameters of the multi-energy spectrum X-ray imaging system under a specific condition using a training sample library for various articles.

2. The method according to claim 1, wherein the specific condition comprises a highest detection rate, a lowest false positive rate, or largest discriminability.

3. The method according to claim 1, wherein the system parameters comprise: an energy value of an X-ray source, a number of divided energy regions and a corresponding energy threshold, a scanning speed, and a radiation dose value.

4. The method according to claim 1, wherein the plurality of parameter modes comprise a first parameter mode for baggage and human body inspection and a second parameter mode for vehicles/containers.

5. The method according to claim 1, further comprising:
   switching the selected parameter mode from the common parameter mode to the high performance parameter mode, when the selected parameter mode is the common parameter mode and it is recognized that there is a high probability of the article being a prohibited article using the selected parameter mode.

6. A multi-energy spectrum X-ray imaging system for recognizing an article, comprising:
   an X-ray source configured to generate X-rays under the control of a scanning controller;
   the scanning controller configured to control the X-ray source according to a selected parameter mode;
   a detector configured to receive X-rays which are emitted from the X-ray source and are transmitted or scattered through the article and convert them into an output signal;
   a processor configured to: recognize an application scenario and/or priori information of the article, select a parameter mode suitable for the article from a plurality of parameter modes stored in the multi-energy spectrum X-ray imaging system based on the recognized application scenario and/or priori information, wherein the plurality of parameter modes comprise a common parameter mode and a high performance parameter mode, and a high performance parameter mode, and receive an output signal from the detector and recognize the article using the output signal; and
   a memory configured to store the plurality of parameter modes,
   wherein the plurality of parameter modes are obtained by optimizing system parameters of the multi-energy spectrum X-ray imaging system under a specific condition using a training sample library for various articles.

7. The system according to claim 6, wherein the specific condition comprises a highest detection rate, a lowest false positive rate, or largest discriminability.

8. The system according to claim 6, wherein the system parameters comprise: an energy value of an X-ray source, a number of divided energy regions and a corresponding energy threshold, a scanning speed, and a radiation dose value.

9. The system according to claim 6, wherein the plurality of parameter modes comprise a first parameter mode for baggage and human body inspection and a second parameter mode for vehicles/containers.

10. The system according to claim 6, wherein the processor is further configured to switch the selected parameter mode from the common parameter mode to the high performance parameter mode, when the selected parameter mode is the common parameter mode and it is recognized that there is a high probability of the article being a prohibited article using the selected parameter mode.

11. A non-transitory computer-readable medium comprising instructions that, when executed by a processor, perform operations of:
   recognizing an application scenario and/or priori information of the article;
   selecting a parameter mode suitable for the article from a plurality of parameter modes stored in the multi-energy spectrum X-ray imaging system based on the recognized application scenario and/or priori information, wherein the plurality of parameter modes comprise a common parameter mode and a high performance parameter mode; and
   recognizing the article using the selected parameter mode, wherein the plurality of parameter modes are obtained by optimizing system parameters of the multi-energy spectrum X-ray imaging system under a specific condition using a training sample library for various articles.

12. The non-transitory computer-readable medium according to claim 11, wherein the specific condition comprises a highest detection rate, a lowest false positive rate, or largest discriminability.

13. The non-transitory computer-readable medium according to claim 11, wherein the system parameters comprise: an energy value of an X-ray source, a number of divided energy regions and a corresponding energy threshold, a scanning speed, and a radiation dose value.

14. The non-transitory computer-readable medium according to claim 11, wherein the plurality of parameter modes comprise a first parameter mode for baggage and human body inspection and a second parameter mode for vehicles/containers.

15. The non-transitory computer-readable medium according to claim 11, further comprising instructions that, when executed by a processor, perform operations of: switching the selected parameter mode from the common parameter mode to the high performance parameter mode, when the selected parameter mode is the common parameter mode and it is recognized that there is a high probability of the article being a prohibited article using the selected parameter mode.

* * * * *